United States Patent
Kester

(10) Patent No.: US 10,842,637 B2
(45) Date of Patent: Nov. 24, 2020

(54) PATELLAR IMPLANT

(71) Applicant: b-ONE Ortho, Corp., Cedar Knolls, NJ (US)

(72) Inventor: Mark A. Kester, Loudon, TN (US)

(73) Assignees: b-ONE Ortho, Corp., Cedar Knolls, NJ (US); b-ONE Medical Biotech Corporation, Shanghai (CN)

( * ) Notice: Subject to any disclaimer, the term of this patent is extended or adjusted under 35 U.S.C. 154(b) by 196 days.

(21) Appl. No.: 16/051,642

(22) Filed: Aug. 1, 2018

(65) Prior Publication Data
US 2020/0038194 A1 Feb. 6, 2020

(51) Int. Cl.
*A61F 2/38* (2006.01)
*A61F 2/30* (2006.01)

(52) U.S. Cl.
CPC ... *A61F 2/3877* (2013.01); *A61F 2002/30112* (2013.01); *A61F 2002/30682* (2013.01); *A61F 2002/30845* (2013.01); *A61F 2002/30889* (2013.01); *A61F 2002/30892* (2013.01); *A61F 2002/30894* (2013.01); *A61F 2002/30897* (2013.01); *A61F 2002/3881* (2013.01)

(58) Field of Classification Search
CPC ............ A61F 2/3877; A61F 2002/3881; A61F 2002/648
USPC .............................................. 623/20.18–20.2
See application file for complete search history.

(56) References Cited

U.S. PATENT DOCUMENTS

| | | | |
|---|---|---|---|
| 5,480,443 A | 1/1996 | Elias | |
| 5,580,353 A | 12/1996 | Mendes et al. | |
| 5,702,465 A | 12/1997 | Burkinshaw | |
| 5,702,467 A | 12/1997 | Gabriel et al. | |
| 6,616,696 B1 | 9/2003 | Merchant | |
| 6,802,864 B2 | 10/2004 | Tornier | |
| 9,289,305 B2 | 3/2016 | Dacus | |
| 9,675,399 B2 | 6/2017 | Ries et al. | |
| 2007/0150066 A1 | 6/2007 | McMinn | |
| 2009/0326662 A1* | 12/2009 | Goldstein | A61F 2/3877 623/20.19 |

(Continued)

FOREIGN PATENT DOCUMENTS

EP 0728450 A2 8/1996

OTHER PUBLICATIONS

International Search Report and Written Opinion dated Oct. 29, 2019 for corresponding PCT Application No. PCT/US2019/042964.

*Primary Examiner* — David H Willse
(74) *Attorney, Agent, or Firm* — Duane Morris LLP

(57) ABSTRACT

A patellar implant includes a body and at least one oblique anchoring pin. The body includes a bone-facing surface that is substantially planar and has a lateral end and a medial end. The body also includes an articulating surface opposite the bone-facing surface. The at least one oblique anchoring pin extends from the bone-facing surface at an acute angle toward the lateral end of the bone-facing surface. The at least one oblique anchoring pin includes a first end attached to the bone-facing surface and a second end spaced from the first end. A longitudinal axis extends from the first end to the second end. The longitudinal axis defines the acute angle with respect to the bone-facing surface. The at least one oblique anchoring pin extends into a surgically-prepared patella when the patellar implant is such that the surgically-prepared patella abuts the bone-facing surface.

18 Claims, 5 Drawing Sheets

(56) References Cited

U.S. PATENT DOCUMENTS

2012/0209393 A1    8/2012  Ries et al.
2015/0320567 A1   11/2015  Terrill et al.
2017/0056180 A1*   3/2017  Schmieding .......... A61F 2/3877
2017/0189194 A1*   7/2017  Klinger ............... A61F 2/30771

* cited by examiner

PATELLAR IMPLANT

FIELD

The application relates to patellar implants for use in knee replacement procedures.

BACKGROUND

In partial knee replacement surgeries, damaged bone of a patient is replaced with metallic or polymeric components to reduce pain and allow for increased mobility. In such a procedure, the underside of the patient's patella and a portion of the patient's femur are resurfaced to allow articulation of the knee joint and reduce or eliminate pain.

The patient's patella is commonly surgically-prepared to provide a smooth or planar surface for contact with the patellar implant. The patellar implant includes one or more features to allow secure attachment to the surgically-prepared patella. These features can include pegs and cavities for bone cement.

SUMMARY

In some embodiments, a patellar implant includes a body and at least one oblique anchoring pin. The body includes a bone-facing surface that is substantially planar and has a lateral end and a medial end. The body also includes an articulating surface opposite the bone-facing surface. The at least one oblique anchoring pin extends from the bone-facing surface at an acute angle toward the lateral end of the bone-facing surface. The at least one oblique anchoring pin includes a first end attached to the bone-facing surface and a second end spaced apart from the first end. A longitudinal axis of the at least one oblique anchoring pin extends from the first end to the second end. The longitudinal axis defines the acute angle with respect to the bone-facing surface. The at least one oblique anchoring pin extends into a surgically-prepared patella when the patellar implant is positioned such that the surgically-prepared patella abuts the bone-facing surface.

In some embodiments, a patellar implant includes a body that comprises a bone-facing surface that is substantially planar having a lateral end and a medial end, and an articulating surface opposite the bone-facing surface; and at least one oblique anchoring pin extending from the bone-facing surface at an acute angle toward the lateral end of the bone-facing surface. The at least one oblique anchoring pin comprises a first end attached to the bone-facing surface; a second end spaced apart from the first end, the second end terminating as a planar surface oriented parallel to the bone-facing surface; and a longitudinal axis extending from the first end to the second end, wherein the longitudinal axis defines the acute angle with respect to the bone-facing surface; wherein the at least one oblique anchoring pin extends into a surgically-prepared patella when the patellar implant is such that the surgically-prepared patella abuts the bone-facing surface.

In another embodiment, a patellar implant includes a body having a bone-facing surface that is substantially planar and has a lateral end and a medial end. The body also has an articulating surface opposite the bone-facing surface. The patellar implant also includes at least one anchoring pin extending from the bone-facing surface. The at least one anchoring pin includes an anterior face spaced apart from the bone-facing surface. The anterior face is oriented at an acute angle toward the lateral end of the bone-facing surface. The at least one anchoring pin extends into a surgically-prepared patella when the patellar implant is positioned such that the surgically-prepared patella abuts the bone-facing surface.

BRIEF DESCRIPTION OF THE DRAWINGS

These and other features and advantages of the patellar implants described herein will be more fully disclosed in, or rendered obvious by, the following detailed description of the preferred embodiments, which is to be considered together with the accompanying drawings wherein like numbers refer to like parts and further wherein.

DETAILED DESCRIPTION

Figure 1:
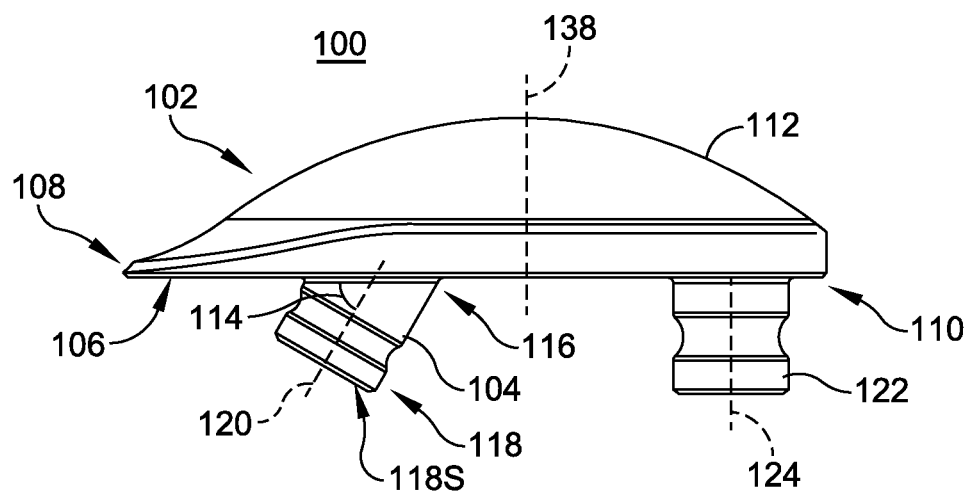
FIG. 1 shows a superior view of a patellar implant according to one embodiment of the present disclosure.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The present disclosure describes patellar implants which include anchoring pins that are configured to anchor the implant to a surgically-prepared patella. The anchoring pins described herein are configured to resist forces imparted on the implant or patella during movement and securely anchor the implant to the surgically-prepared patella. As described further herein, the anchoring pins are configured to resist displacement from the patella when a laterally directed force is applied to the patella, as is common during walking. In addition, embodiments of the patellar implants described herein also include cavities for receiving bone cement that are oriented to provide additional resistance to disengagement of the patellar implant from the patella.

In a first embodiment, as shown in FIGS. 1-4, a patellar implant 100 includes a body 102 and at least one oblique anchoring pin 104 extending from the body 102. The body 102 includes a bone-facing surface 106 that, in at least one embodiment, is substantially planar. The bone-facing surface 106 has a lateral end 108 and a medial end 110. The body 102 also includes an articulating surface 112 opposite the bone-facing surface 106. The articulating surface 112 is configured for contact with the femur of the patient or a femoral implant and is contoured to allow smooth articulation.

The oblique anchoring pin 104 extends from the bone-facing surface 106 at an acute angle 114 toward the lateral end 108 of the bone-facing surface 106. The oblique anchoring pin includes a first end 116 attached to the bone-facing surface 106 and a second end 118 spaced apart from the first end 116 and the bone-facing surface 106. A longitudinal axis 120 of the at least one oblique anchoring pin 104 extends from the first end 116 to the second end 118 and the longitudinal axis 120 defines the acute angle 114 with respect to the bone-facing surface 106. In the embodiment shown in FIGS. 1 and 2A, the second end 118 of the oblique anchoring pin 104 terminates with a planar surface 118S that is orthogonal to the longitudinal axis 120. The oblique anchoring pin 104 extends into a surgically-prepared patella when the patellar implant 100 is such that the surgically-prepared patella abuts the bone-facing surface 106.

Figure 2A:
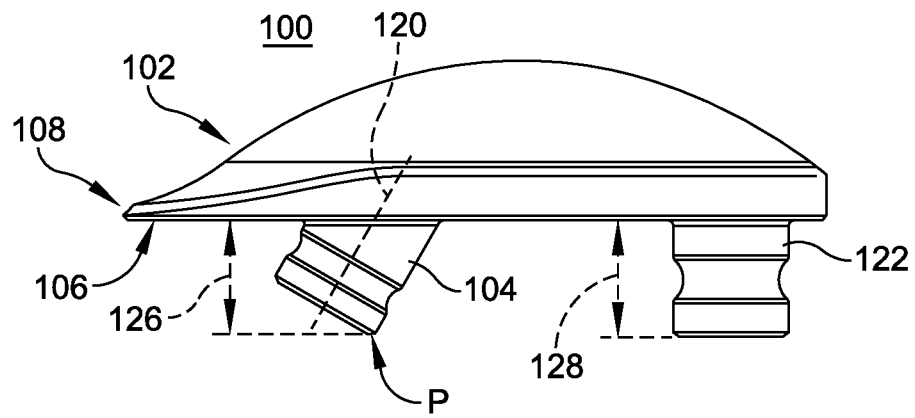
FIG. 2A shows an additional superior view of the patellar implant of FIG. 1.
Figure 2B:
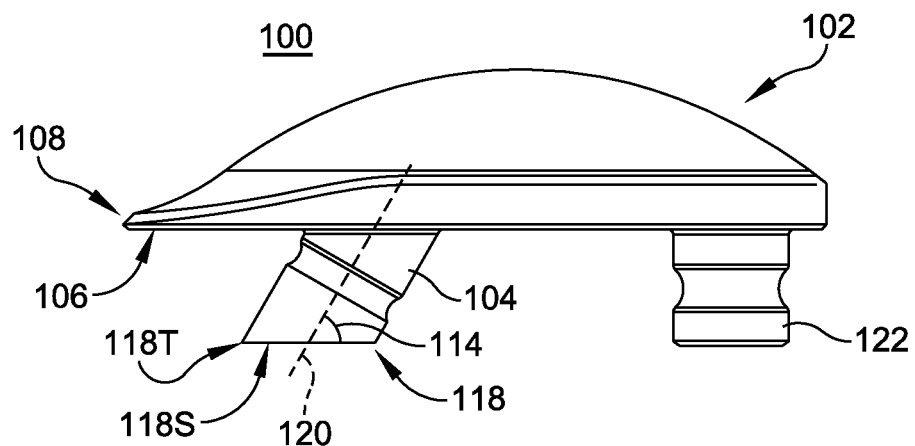
FIGS. 2B, 2C, 2D, and 2E show superior views of patellar implants according to some other embodiments.

As shown in FIG. 2A, the oblique anchoring pin 104 has a maximum height 126 measured from the bone-facing surface 106. Further, the orthogonal anchoring pin 122 has a maximum height 128 measured from the bone-facing surface 106 to the point P, the furthest point from the bone-facing surface 106. In one embodiment, the maximum height 126 of the oblique anchoring pin 104 is equal to the maximum height 128 of the orthogonal anchoring pin 122.

During walking, the quadriceps muscle group imparts a laterally directed force on the patella. By providing the at least one oblique anchoring pin 104 that is oriented at the acute angle 114 toward the lateral end 108, the oblique anchoring pin 104 digs into the patella bone when the patellar implant 100, that is implanted into a patient, is subjected to a lateral force from the quadriceps muscles during the patient's walking motion. That enhances the securement between the patellar implant 100 and the patella bone and decreases the risk of disengagement of the patellar implant 100 from the patella.

In the embodiment shown in FIG. 2A, the shape of the second end 118 of the oblique anchoring pin 104 is similar to that of the orthogonal anchoring pin 122. However, the obliquely angled disposition of the oblique anchoring pin 104 enhances the securement between the patellar implant 100 and the patella bone. The oblique angle allows the oblique anchoring pin 104 to bite into the patella bone and prevent or minimize any lateral displacement when the patellar implant 100 is urged in the lateral direction by the quadriceps muscle group during walking.

In some embodiments, the second end 118 of the oblique anchoring pin 104 can be configured with a variety of different shapes in order to enhance the oblique anchoring pin's ability to prevent or minimize lateral displacement of the implant during the patient's walking motion. For example, referring to FIG. 2B, in some embodiments, the planar surface 118S at the second end 118 of the oblique anchoring pin 104 is oriented parallel to the bone-facing surface 106. In this embodiment, because the planar surface 118S is parallel to the bone-facing surface 106, the planar surface 118S forms the same acute angle 114 with the longitudinal axis 120 of the oblique anchoring pin 104. Because the planar surface 118S at the second end 118 of the oblique anchoring pin 104 is parallel to the bone-facing surface 106, the planar surface 118S and the sidewall of the oblique anchoring pin 104 on the side closer to the lateral end 108 forms a tip 118T that has a wedge shaped profile. This wedge shaped tip 118T further assists the oblique anchoring pin 104 to bite into the patella bone and prevent any lateral displacement of the patellar implant 100 when the patellar implant 100 is urged in the lateral direction by the quadriceps muscle group during walking.

Figure 2C:
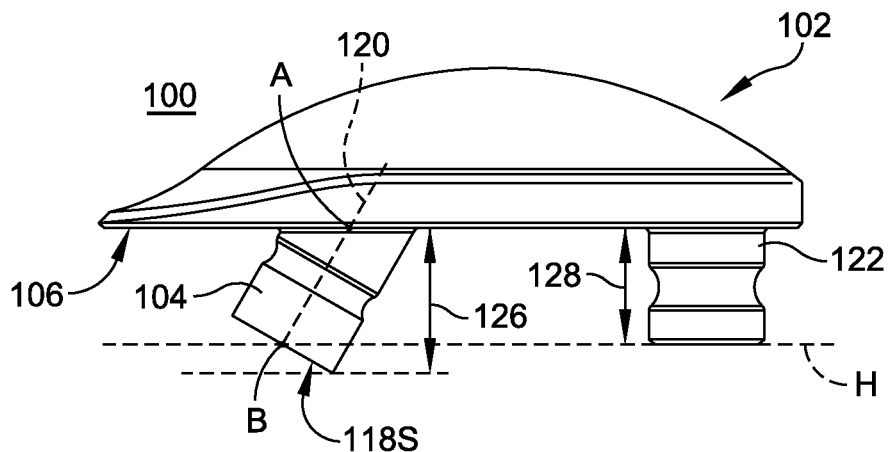

In an example shown in FIG. 2C, the planar surface 118S of the oblique anchoring pin 104 is orthogonal to the longitudinal axis 120 similar to the embodiment shown in FIG. 2A. However, in the embodiment in FIG. 2C, the oblique anchoring pin 104 is longer than the orthogonal anchoring pin 122 and longer than the embodiment of the oblique anchoring pin 104 of FIG. 2A. The length of the oblique anchoring pin 104 refers to the distance between point A where the longitudinal axis 120 intersects the bone-facing surface 106 and point B where the longitudinal axis 120 intersects the plane H that is parallel to the bone-facing surface 106 and positioned at a distance from the bone-facing surface 106 that is equal to the maximum height 128 of the orthogonal anchoring pin 122. This also results in the maximum height 126 of the oblique anchoring pin 104 measured from the bone-facing surface 106 is longer than the maximum height 128 of the orthogonal anchoring pin 122 measured from the bone-facing surface 106. In this embodiment, the combination of the oblique disposition and the length of the oblique anchoring pin 104 enable the ability of the patellar implant 100 to prevent or minimize any lateral displacement.

Figure 2D:
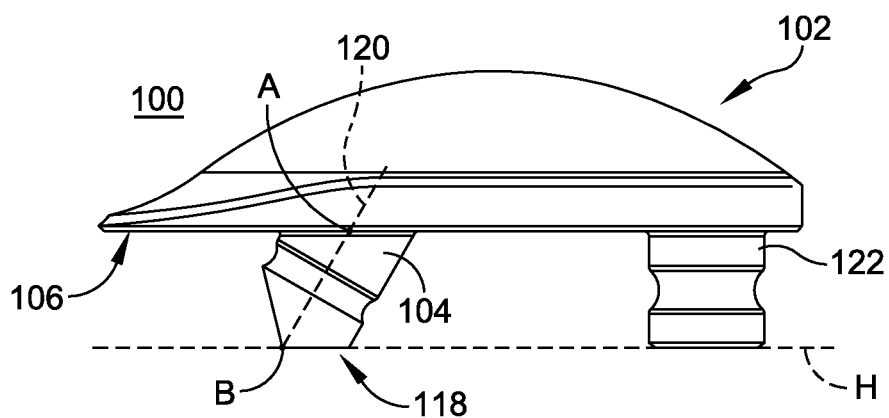
Figure 2E:
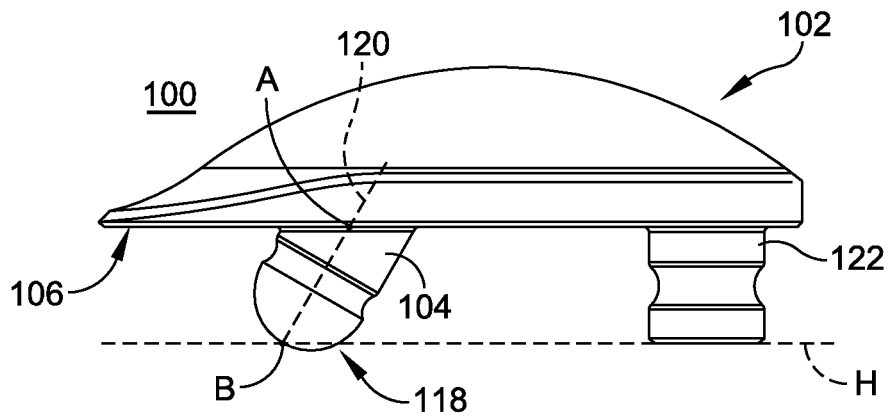

FIGS. 2D and 2E show some additional examples where the length of the oblique anchoring pin 104 as measured between the point A and point B is the same as that of the embodiment shown in FIG. 2C. However, in the embodiments of FIGS. 2D and 2E, the second end 118 of the oblique anchoring pin 104 does not terminate in a planar surface 118S but in other desired shape. For example, in the embodiment of FIG. 2D, the second end 118 of the oblique anchoring pin 104 has a pointed profile. In the embodiment of FIG. 2E, the second end 118 of the oblique anchoring pin 104 has a rounded or spherical shape. These embodiments also provide the ability for the patellar implant 100 to prevent or minimize any lateral displacement because of the oblique anchoring pin's oblique disposition.

The patellar implant 100 can include any number of oblique anchoring pins 104. In one embodiment, the patellar implant 100 includes two oblique anchoring pins 104. Each of the oblique anchoring pins 104 has a longitudinal axis 120 that intersects the bone-facing surface 106 at the acute angle 114. In one such embodiment, the respective intersections between the longitudinal axis 120 and the bone-facing surface 106 are equally spaced from the lateral end 108 of the bone-facing surface 106.

In one embodiment, the patellar implant 100 further includes one or more orthogonal anchoring pin 122 that extends from the bone-facing surface 106 in an orthogonal direction such that a longitudinal axis 124 of the orthogonal anchoring pin 122 is orthogonal to the bone-facing surface 106. The patellar implant 100 can include any number of orthogonal anchoring pins 122. In one embodiment, the patellar implant includes one orthogonal anchoring pin 122. In another embodiment, the patellar implant 100 includes two orthogonal anchoring pins 122. In another embodiment, the patellar implant 100 includes three orthogonal anchoring pins 122.

Figure 3:
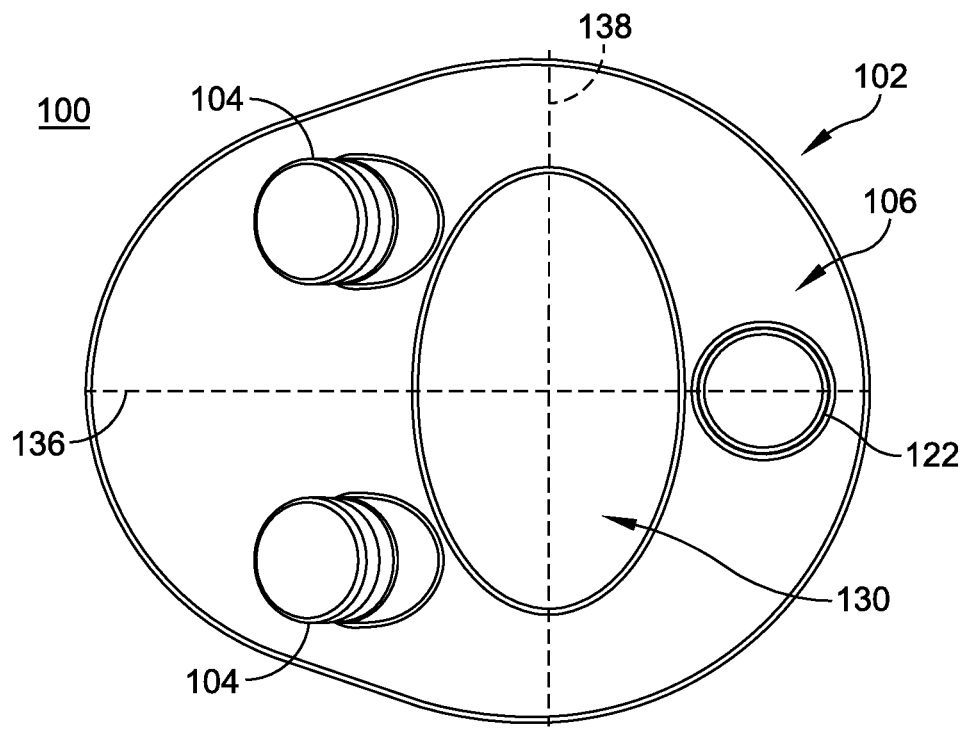
FIG. 3 shows an anterior view of the patellar implant of FIG. 1.
Figure 4:
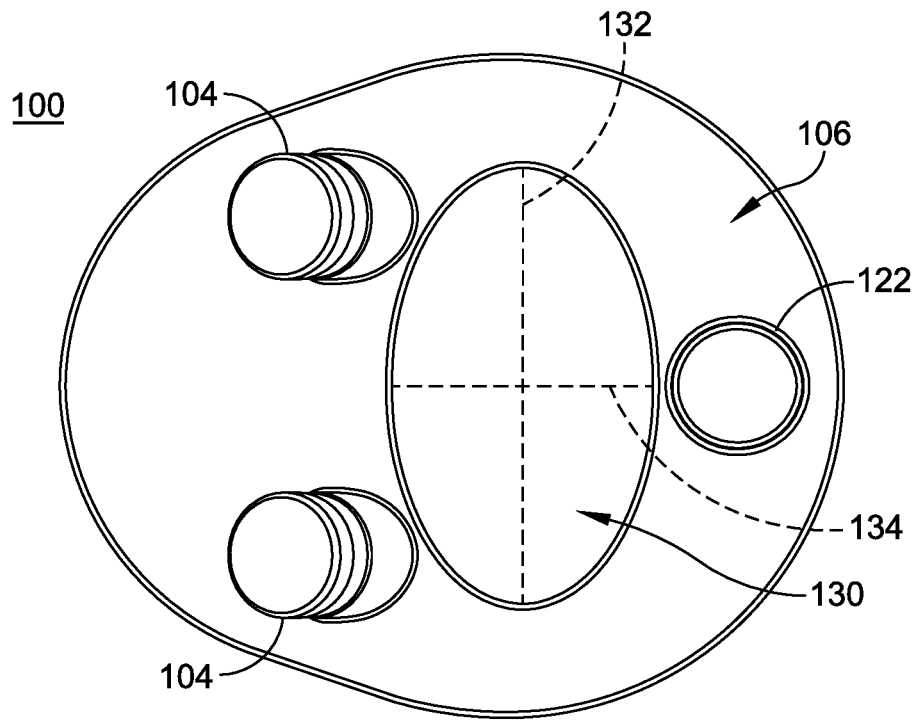
FIG. 4 shows another anterior view of the implant of FIG. 1

Referring to FIGS. 3 and 4, viewing from the bone-facing surface 106, the body 102's medial-lateral axis 136 extending from the medial end 110 to the lateral end 108 of the bone-facing surface 106 is identified in FIG. 3. The body 102 can further include a cavity 130 extending into the bone-facing surface 106. The cavity 130 is configured for receiving bone cement to secure the patellar implant 100 to the surgically-prepared patella. In one embodiment, the cavity 130 has an oval-shaped outline. The oval-shaped outline has a major axis 132 and a minor axis 134. The oval-shaped cavity 130 is oriented such that the major axis 132 is preferably perpendicular to the medial-lateral axis 136 of the bone-facing surface 106.

In other embodiments, the outline of the cavity 130 is in the form of a shape other than an oval. For example, the cavity can have a rectangular-shaped outline. In such an embodiment, the cavity 130 has a first length that is perpendicular to the medial-lateral axis 136 of the bone-facing surface and a second length that is parallel to the medial-lateral axis 136. In at least one embodiment, the first length is longer than the second length. By orienting the cavity 130 in this way the lateral wall of cement that is resisting the lateral shear on the patella implant 100 is increased. This can further reduce the risk of disengagement from the patella.

The articulating surface 112 of the implant 100 can be configured with any appropriate shape and contour to provide the desired interface with the patient's femur or a femoral implant. For example, in one embodiment, the articulating surface 112 is symmetric about a plane 138 (the plane 138 is shown in FIG. 1) that is orthogonal to the medial-lateral axis 136. In another embodiment, the articulating surface 112 is asymmetric about the plane 138 as shown in the embodiment of the implant 100 shown in FIGS. 1 and 2.

Figure 5:
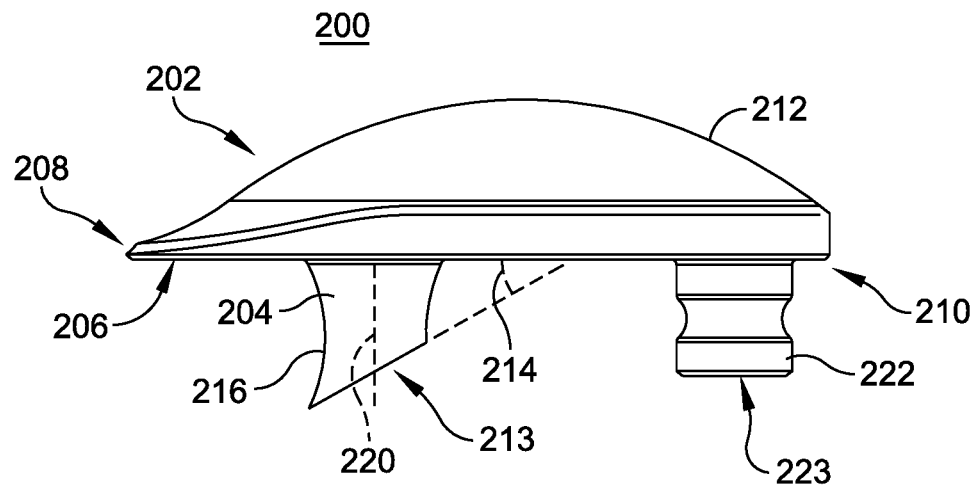
FIG. 5 shows a superior view of a patellar implant according to another embodiment of the present disclosure.
Figure 6:
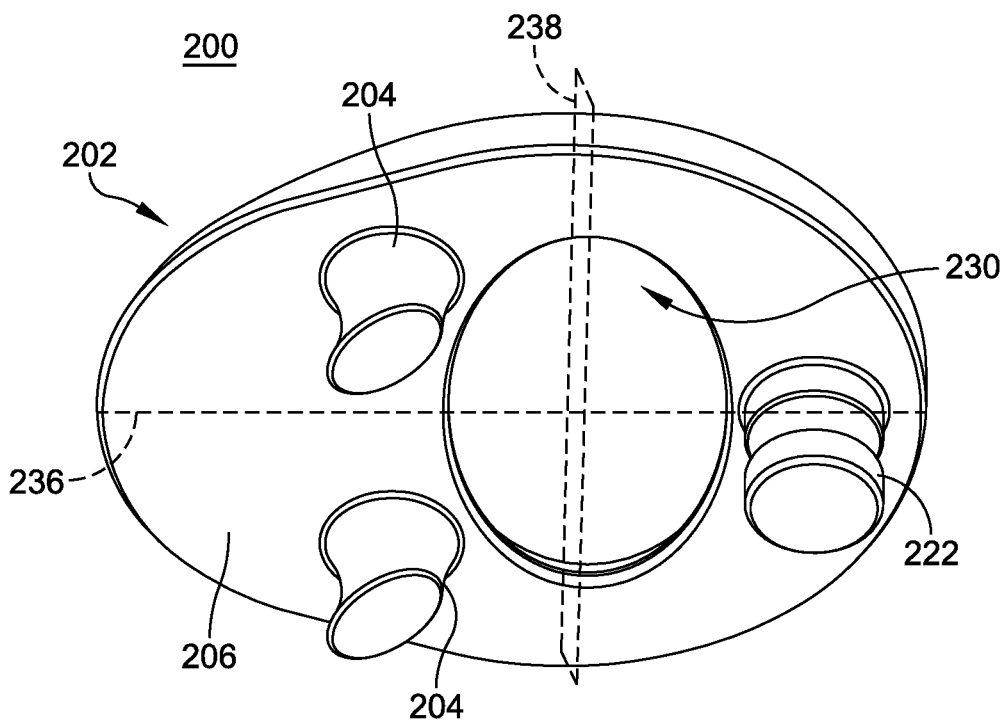
FIG. 6 shows a perspective anterior view of the patellar implant of FIG. 5.
Figure 7:
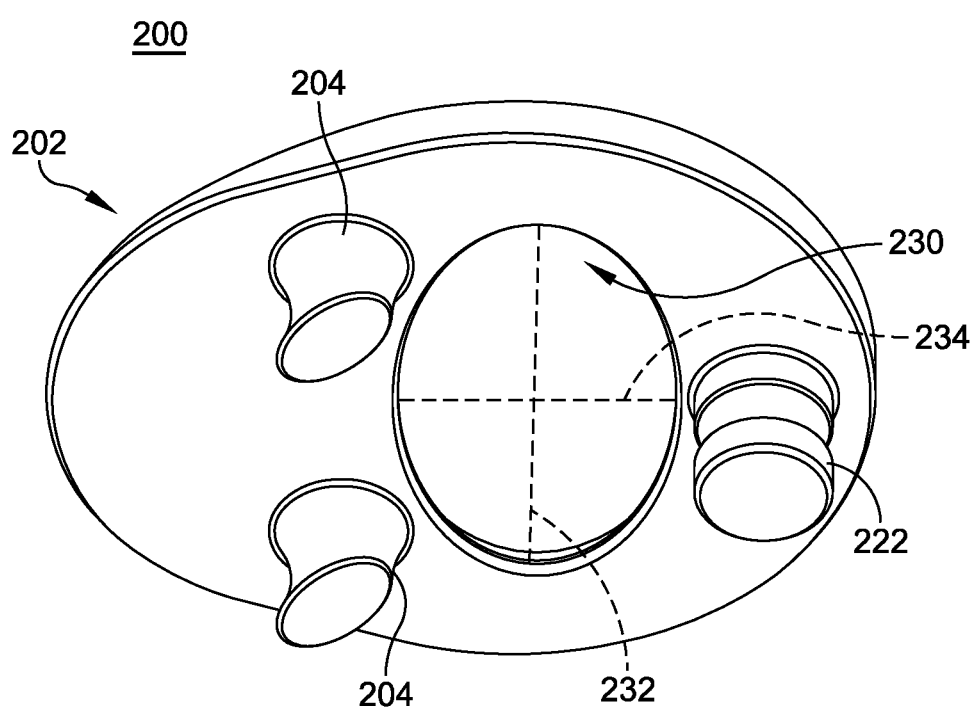
FIG. 7 shows an additional perspective anterior view of the patellar implant of FIG. 5.

In another embodiment, shown in FIGS. 5-7, a patellar implant 200 includes a body 202 having a bone-facing surface 206 that is substantially planar and has a lateral end 208 and a medial end 210. The implant 200 also includes at least one anchoring pin 204 extending from the bone-facing surface 206. The body 202 also includes an articulating surface 212 opposite the bone-facing surface 206. The articulating surface 212 is configured for contact with the femur of the patient or a femoral implant and is contoured to allow smooth articulation.

The anchoring pin 204 extends from the bone-facing surface 206 and includes an anterior face 213 spaced apart from the bone-facing surface 206. The anterior face 213 is oriented at an acute angle 214 toward the lateral end 208 of the bone-facing surface 206. The anchoring pin 204 extends into a surgically-prepared patella when the patellar implant 200 is positioned such that the surgically-prepared patella abuts the bone-facing surface. The anchoring pin 204 includes a sidewall 216 extending from the bone-facing surface 206 to the anterior face 213. In one embodiment, the sidewall 216 is concave. The combination of the angled anterior face 213 and the concave sidewall 216 of the anchoring pin 204 allows the anchoring pin 204 to dig into the patella bone when the patellar implant 200, that is implanted into a patient, is subjected to a lateral force from the quadriceps muscles during the patient's walking motion. That enhances the securement between the patellar implant 200 and the patella bone and decreases the risk of disengagement of the patellar implant 200 from the patella, as described above with respect to the patellar implant 100.

The patellar implant 200 can include any number of anchoring pins 204. In one embodiment, the patellar implant 200 includes two anchoring pins 204. Each of the anchoring pins 204 have a longitudinal axis 220 that forms an intersection with the bone-facing surface 206. In one such embodiment, the respective intersections are equally spaced from the lateral end 208 of the bone-facing surface 206.

As shown in FIGS. 6 and 7, the body 202 further includes a cavity 230 extending into the bone-facing surface 206. The cavity 230 is configured for receiving bone cement to secure the patellar implant 200 to the surgically-prepared patella. In one embodiment, the cavity 230 has an oval-shaped outline. The oval-shaped outline has a major axis 232 and a minor axis 234 (shown in FIG. 7). The major axis 232 is perpendicular to a medial-lateral axis 236 (shown in FIG. 6) that extends from the medial end 210 of the bone-facing surface 206 to the lateral end 208 of the bone-facing surface 206. This configuration of the cavity 230 further enhances the engagement of the patellar implant 200 and the patella and resists laterally oriented forces, as described above.

In other embodiments, the outline of the cavity 230 is in the form of a shape other than an oval. For example, the cavity can have a rectangular-shaped outline. In such an embodiment, the cavity 230 has a first length that is perpendicular to the medial-lateral axis 236 of the bone-facing surface and a second length that is parallel to the medial-lateral axis 236. In at least one embodiment, the first length is longer than the second length.

The articulating surface 212 can be configured with any appropriate shape and contour to provide the desired interface with the patient's femur or a femoral implant. For example, in one embodiment, the articulating surface 212 is symmetric about a plane 238 (shown in FIG. 6) that is orthogonal to the medial-lateral axis 236. In another embodiment, the articulating surface 212 is asymmetric about the plane 238.

The patellar implant 200 can also include one or more secondary anchoring pins 222 that have an anterior face 223 that is substantially parallel to the bone-facing surface 206. Further, the secondary anchoring pin 222 includes a sidewall having a concave portion. The patellar implant 200 can include any number of secondary anchoring pins 222 positioned at any location on the bone-facing surface 206. As shown in FIGS. 5-7, in one embodiment, the secondary anchoring pin 222 is positioned medially from the anchoring pins 204.

The patellar implants 100, 200 can be constructed in a single monolithic component. Alternatively, the patellar implants 100, 200 can be constructed of two or more components that are joined together using bonding, welding, press-fit, or any other appropriate process. For example, the anchoring pins can be joined to the body by bonding. Further, the patellar implants 100, 200 described herein can be constructed of any appropriate material. For example, the patellar implants 100, 200 can be constructed of polyethylene.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

What is claimed is:

1. A patellar implant comprising:
    a body comprising:
        a bone-facing surface that is substantially planar having a lateral end and a medial end, and
        an articulating surface opposite the bone-facing surface;
    at least one orthogonal anchoring pin that extends from the bone-facing surface in an orthogonal direction, whereby the orthogonal anchoring pin's longitudinal axis is orthogonal to the bone-facing surface; and
    at least one oblique anchoring pin extending from the bone-facing surface at an acute angle toward the lateral end of the bone-facing surface, the at least one oblique anchoring pin comprising:
        a first end attached to the bone-facing surface,
        a second end spaced apart from the first end, and
        a longitudinal axis extending from the first end to the second end, wherein the longitudinal axis defines the acute angle with respect to the bone-facing surface;
    wherein the at least one oblique anchoring pin extends into a surgically-prepared patella when the patellar implant is positioned such that the surgically-prepared patella abuts the bone-facing surface.

2. The patellar implant of claim 1, wherein the at least one oblique anchoring pin has a first maximum height measured from the bone-facing surface and the at least one orthogonal anchoring pin has a second maximum height measured from the bone-facing surface, wherein the first maximum height and the second maximum height are equal.

3. The patellar implant of claim 1, comprising at least two oblique anchoring pins that extend in the same direction from the bone-facing surface at an acute angle toward the lateral end of the bone-facing surface.

4. The patellar implant of claim 3, wherein the at least two oblique anchoring pins each having a longitudinal axis that forms an intersection with the bone-facing surface, and wherein the respective intersections are equally spaced from the lateral end of the bone-facing surface.

5. The patellar implant of claim 1, wherein the body further includes a cavity for receiving bone cement extending into the bone-facing surface.

6. The patellar implant of claim 5, wherein the cavity has an oval-shaped outline, the oval shape having a major axis and a minor axis, wherein the major axis is perpendicular to a medial-lateral axis that extends from the medial end of the bone-facing surface to the lateral end of the bone-facing surface.

7. The patellar implant of claim 5, wherein the cavity has a first length perpendicular to a medial-lateral axis that extends from the medial end of the bone-facing surface to the lateral end of the bone-facing surface and a second length that is parallel to the medial-lateral axis, and wherein the first length is longer than the second length.

8. The patellar implant of claim 1, wherein the articulating surface is symmetric about a plane orthogonal to a medial-lateral axis that extends from the medial end of the bone-facing surface to the lateral end of the bone-facing surface.

9. The patellar implant of claim 1, wherein the articulating surface is asymmetric about a plane orthogonal to a medial-lateral axis that extends from the medial end of the bone-facing surface to the lateral end of the bone-facing surface.

10. A patellar implant comprising:
    a body comprising:
        a bone-facing surface that is substantially planar having a lateral end and a medial end, and
        an articulating surface opposite the bone-facing surface;
    at least one orthogonal anchoring pin that extends from the bone-facing surface in an orthogonal direction, whereby the orthogonal anchoring pin's longitudinal axis is orthogonal to the bone-facing surface; and
    at least one oblique anchoring pin extending from the bone-facing surface at an acute angle toward the lateral end of the bone-facing surface, the at least one oblique anchoring pin comprising:
        a first end attached to the bone-facing surface;
        a second end spaced apart from the first end, the second end terminating as a planar surface oriented parallel to the bone-facing surface; and
        a longitudinal axis extending from the first end to the second end, wherein the longitudinal axis defines the acute angle with respect to the bone-facing surface;
    wherein the at least one oblique anchoring pin extends into a surgically-prepared patella when the patellar implant is positioned such that the surgically-prepared patella abuts the bone-facing surface.

11. The patellar implant of claim 10, wherein the at least one oblique anchoring pin has a first maximum height measured from the bone-facing surface and the at least one orthogonal anchoring pin has a second maximum height measured from the bone-facing surface, wherein the first maximum height and the second maximum height are equal.

12. The patellar implant of claim 10, comprising at least two oblique anchoring pins that extend in the same direction from the bone-facing surface at an acute angle toward the lateral end of the bone-facing surface.

13. The patellar implant of claim 12, wherein the at least two oblique anchoring pins each having a longitudinal axis that forms an intersection with the bone-facing surface, and wherein the respective intersections are equally spaced from the lateral end of the bone-facing surface.

14. The patellar implant of claim 10, wherein the body further includes a cavity for receiving bone cement extending into the bone-facing surface.

15. The patellar implant of claim 14, wherein the cavity has an oval-shaped outline, the oval shape having a major axis and a minor axis, wherein the major axis is perpendicular to a medial-lateral axis that extends from the medial end of the bone-facing surface to the lateral end of the bone-facing surface.

16. The patellar implant of claim 14, wherein the cavity has a first length perpendicular to a medial-lateral axis that extends from the medial end of the bone-facing surface to the lateral end of the bone-facing surface and a second length that is parallel to the medial-lateral axis, and wherein the first length is longer than the second length.

17. The patellar implant of claim 10, wherein the articulating surface is symmetric about a plane orthogonal to a medial-lateral axis that extends from the medial end of the bone-facing surface to the lateral end of the bone-facing surface.

18. The patellar implant of claim 10, wherein the articulating surface is asymmetric about a plane orthogonal to a medial-lateral axis that extends from the medial end of the bone-facing surface to the lateral end of the bone-facing surface.

* * * * *